United States Patent [19]

Ansari et al.

[11] 3,959,455
[45] May 25, 1976

[54] LABELING OF INDOCYANINE GREEN WITH CARRIER-FREE IODINE-123

[75] Inventors: Azizullah N. Ansari, Mount Sinai; Richard M. Lambrecht, East Quogue; Carol S. Redvanly, Upton; Alfred P. Wolf, East Setauket, all of N.Y.

[73] Assignee: The United States of America as represented by the United States Energy Research and Development Administration, Washington, D.C.

[22] Filed: July 1, 1975

[21] Appl. No.: 592,305

[52] U.S. Cl. .............. 424/1; 252/301.1 R; 260/240.5
[51] Int. Cl.$^2$ .............. A61K 43/00; C09B 23/08
[58] Field of Search ............ 424/1; 260/240.5; 252/301.1 R

[56] References Cited
OTHER PUBLICATIONS

Chrostowski, Chemical Abstracts, Vol. 73, No. 21, Nov. 23, 1970, p. 179, Abstract No. 107396t.

Reuter et al., Chemical Abstracts, Vol. 72, No. 5, Feb. 2, 1970, p. 145, Abstract No. 19953w.

Bassir et al., Chemical Abstracts, Vol. 81, No. 23, Dec. 9, 1974, p. 211, Abstract No. 148071s.

Mikulecky et al., Chemical Abstracts, Vol. 77, No. 9, Aug. 28, 1972, pp. 308–309, Abstract No. 59607w.

*Primary Examiner*—Benjamin R. Padgett
*Assistant Examiner*—Christine M. Nucker
*Attorney, Agent, or Firm*—Dean E. Carlson; Leonard Belkin

[57] ABSTRACT

The method of labeling indocyanine green (ICG) with carrier-free iodine-123 comprising the steps of condensing xenon-123 on crystals of ICG followed by permitting decay of the $^{123}$Xe a sufficient length of time to produce $^{123}$I-electronically excited ions and atoms which subsequently label ICG.

4 Claims, No Drawings

LABELING OF INDOCYANINE GREEN WITH CARRIER-FREE IODINE-123

BACKGROUND OF THE INVENTION

The invention described herein was made in the course of, or under a contract with the U.S. Atomic Energy Commission and/or the U.S. Energy Research and Development Administration.

The medicinal use of dyes was appreciated as early as 1890, when methylene blue was recommended as an intestinal antiseptic. Since then various dyes have been used as diagnostic as well as therapeutic agents.

In 1909, halogenated phthaleins were introduced for the study of hepatic physiology. Various dyes were investigated until in 1925 the advantages of bromsulphalein (BSP) were reported as a test of hepatic function. Although the BSP liver function test is considered a sensitive one, it has severe limitations.

In 1924 Rose Bengal was introduced as a liver function test. Rose Bengal is taken up by, and stored in the hepatic polygonal cells rather than in the Kupffer cells of the liver. It has a smaller ratio of extrahepatic clearance than that of BSP. In 1955, $^{131}$I-labeled Rose Bengal was described as an agent for the determination of liver function. The $^{131}$I-Rose Bengal test has been modified by various investigators but the use of radiolabeled Rose Bengal in the differential diagnosis of jaundice has not been universally accepted.

Another dye which has been commonly used for hepatic function tests is indocyanine green (ICG). This dye is exclusively extracted and stored by polygonal cells of the liver before it is excreted into the bile. This dye has no extrahepatic extraction and in tests conducted no ICG was detected in the urine of hepatectomized dogs nor in dogs or rats with biliary obstruction.

ICG has been extensively used in dye dilution curves applied to cardiac output measurement, coronary flow and for continuous recording of blood flow in the limbs. Since its introduction in 1957 it has been used in the study of hemodynamic changes during hemodialysis, measurements of pulmonary shunts, evaluation of the severity and progression of shock, angiography of the oculochoroidal circulation, estimation of blood volume, and as a test for determination of hepatic function.

Taking the foregoing into consideration, it is apparent that indocyanine green could be useful as a labelled compound for hepatic functional evaluation provided some means can be found to label it suitably for such use.

Heretofore, it has not been possible to label ICG with a radio-nuclide capable for use in medical diagnosis.

SUMMARY OF THE INVENTION

The present invention provides for the labelling of indocyanine green (ICG) with carrier-free $^{123}$I to produce a radiopharmaceutical which is suitable for the dynamic imaging of the hepatobiliary system. It has been demonstrated that $^{123}$I-ICG behaves the same biologically and physiologically as unlabeled ICG.

In accordance with a preferred embodiment of this invention, indocyanine green is labeled with carrier-free iodine-123 by the steps of condensing under evacuated conditions Xenon-123 on dry crystals of substantially pure ICG, permitting decay of the Xenon-123 for sufficient time to produce a predetermined amount of $^{123}$I, and subsequently separating the ICG-$^{123}$I from any inorganic radioiodine present. By substantially pure ICG herein is meant that any undesired impurities present are not detectable by the usual detection methods involved for such products.

In the event the starting ICG reagent contains some free iodide (i.e., NaI), the latter may be removed by dissolving the ICG in methyl or ethyl alcohol and then passing the solution through an ion retardation resin.

The labeling method is termed excitation labeling, and results in a random label in the ICG. The position of iodine-123 label in the dye is random and undefined. Thin layer chromatography indicates that at least two radioactive organic compounds are present in $^{123}$I-ICG, but the integrity of the ICG molecule is maintained. The free inorganic (non-organically bound) $^{123}$I is removed from the $^{123}$I-ICG. Free Iodine-123 in the chemical form as iodide is ≤ 0.2%.

It is thus a principal object of this invention to label ICG with carrier-free iodine-123.

Other objects and advantages of this invention will hereinafter become obvious from the following description of preferred embodiments of this invention.

DESCRIPTION OF THE PREFERRED EMBODIMENTS

For use in this invention, $^{123}$Xe may be produced via any appropriate nuclear reaction. The $^{122}$Te $(\alpha,3n)$ $^{123}$Xe nuclear reaction, or, alternatively, the $^{127}$I$(p,5n)$ $^{123}$Xe reaction were employed for this invention. The method of production of $^{123}$Xe does not affect the labeling procedure.

Repurified, dried, crystalline ICG is placed in a reaction vessel which is then evacuated and maintained at a temperature at or below the condensing temperature of the $^{123}$Xe for the evacuated conditions. This may be accomplished by employing a liquid nitrogen bath, i.e., 77°K. The carrier-free $^{123}$Xe is then introduced to the vessel where the reagent is condensed on the crystals of the ICG. Iodine-123 atoms and $^{123}$I-electronically excited ions resulting from the decay of $^{123}$Xe via the nuclear transformation

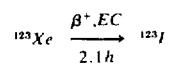

$$^{123}Xe \xrightarrow[2.1h]{\beta^+,EC} {}^{123}I$$

are the labeling species.

The $^{123}$Xe is permitted to decay under the conditions under which it was condensed for a sufficient period of time to produce the amount of $^{123}$I desired.

The remaining $^{123}$Xe is then removed by warming the ICG to a temperature above that of the boiling temperature of the $^{123}$Xe (this may be done merely by removing the liquid nitrogen bath and permitting the reaction vessel to warm up to ambient temperature).

The labeled ICG is then dissolved in ethyl or methyl alcohol, and any $^{123}$I present is removed by passing the solution through an ion retardation resin column prepared for retarding the iodide. It may be necessary to pass the solution through two or more columns to remove all the iodide. The alcohol is then evaporated and the $^{123}$I-ICG is ready for application after dissolution in sterile water for injection.

The amount of ICG which is employed depends, of course, on the amount desired for use. The amount of $^{123}$Xe which is condensed depends on the amount and specific activity of $^{123}$I which is desired. The latter is determined by the specific application. For example, it is expected that $^{123}$Xe would be employed in the range of 0.1 to 1000 mCi per mg. of ICG. Sufficient $^{123}$Xe would be employed to produce a specific activity greater than 0.1 mCi of $^{123}$I per mg. of ICG. These are variables which can be varied as understood by those skilled in the art to produce the degree of activity desired for any particular application.

EXAMPLES

The 60 inch cyclotron at Brookhaven National Laboratory was used to produce $^{123}$Xe via the $^{122}$Te $(\alpha,3n)$ $^{123}$Xe nuclear reaction, and the Brookhaven Linac was employed for the $^{127}$I $(p,5n)$ $^{123}$Xe reaction.

50 mg. of Indocyanine Green, U.S.P. (Cardio-green, a registered trademark, as supplied by Hynson, Westcott and Dunning, Inc. Baltimore, Md. was purified to remove the sodium iodide adulterant, by dissolution of the dye in 3–5 ml of anhydrous absolute methanol, and passage of the solution successively through two glass columns (2 cm × 2 cm) that contained prewashed analytical grade ion retardation resin (AG 11A8, 50 -100 mesh, Bio-Rad Labs, Richmond, Ca). The alcohol in the repurified ICG was removed. The ICG was dried and stored under vacuum until use for labeling. The level of stable iodine contaminant in the ICG was below the limits of chemical detection.

EXAMPLE 1

0.39 mg of the dried ICG was placed on the bottom of a dried, prewashed glass reaction vessel, to which a plug of glass wool was placed on top of the crystals. The vessel was evacuated to ~20 microns total pressure. Radioactive xenon-123 was condensed onto the ICG crystals by cooling the tip of the reaction vessel with liquid nitrogen (77°K). The reaction vessel was kept at a temperature below the boiling point of xenon (−167.1°C) for 12 hrs while the xenon-123 decayed to iodine-123. The iodine-123 subsequently reacted in situ with the ICG (i.e. an excitation labeling mechanism), subsequently the remaining radioxenons were removed by vacuum pumping. The seal to the reaction vessel was broken. The inorganic chemical forms of iodine-123, and the organically bound iodine-123, and the unlabeled ICG were taken into solution with 3 ml of absolute anhydrous ethanol, passed through two columns (2 cm × 28 cm) containing ion retardation resin (AG 11A8, Bio-Rad Labs) that had been autoclaved and prewashed with sterile, pyrogen-free water. The dye was eluted with absolute ethanol, the eluent ~10 ml containing the carrier-free randomly iodine-123 labeled $^{123}$I-ICG was taken to dryness in a 25 ml flask by heating the solution in a water bath at 100°C, while blowing a stream of nitrogen into the solvent. The dried product (0.3 mg, 77% chemical recovery) was taken into solution by addition of sterile aqueous solvent (HW&D), and then sterilized by passage through a 0.22 μm size millipore filter. The overall radiochemical yield for iodine-123 utilized in the synthesis was 8.56%. The specific activity at the completion of the preparation was 5.79 mCi per mg of indocyanine green. The final product at end of preparation contained 1.7 mCi of carrier-free iodine-123 labeled indocyanine green. The $^{123}$ I-ICG was tested for appropriate biological behavior, and also tested and found to be sterile and pyrogen-free, as required for a radiopharmaceutical suitable for intravenous injection. The total time required after the period of xenon-123 decay was 35 minutes. A total of 232 mCi of iodine-123 calculated to the end of xenon-123 production was used. The specific activity in the product is necessarily determined by the total time that the xenon-123 (T½ = 2.1 hr.) and iodine-123 (T½ = 13.1 hr) is allowed to decay before the labeled compound is used.

EXAMPLE 2

The same procedure as described in example 1, except 1.85 mg of indocyanine green was used for the labeling, and the dissolution of the iodine-123 and iodine-123 labeled indocyanine green was affected by addition of 5 ml of absolute anhydrous methanol, instead of absolute ethanol. The overall chemical recovery of ICG was 85%. The radiochemical yield was 12.9%. The final product at the end of preparation contained 3.5 mCi of carrier-free iodine-123 labeled indocyanine green, which represented a specific activity of 2.23 mCi/mg. A total of 120 mCi of iodine-123 calculated to the end of production of xenon-123 was used. The specific activity in the product is necessarily determined by the total time that the xenon-123 (T½ = 2.1 hr) and iodine-123 (T½ = 13.1 hr) is allowed to decay before the labeled compound is used.

The reason for removal of the stable bulk sodium iodide present in 2–5% concentration in the ICG (U.S.P) is that the only reported adverse reactions to the non-radioactive compound have been ascribed to the presence of iodide; and if free stable iodine is present during the labeling process, the iodine-123 exchanges with it, and if injected with the iodine-123 labeled $^{123}$I-ICG, the inorganic radioactive iodine-123 in the chemical form as iodide accumulates in the thyroid gland, negating the usefulness of $^{123}$I-ICG as a radiopharmaceutical.

Additional information and details relating to the method described above appear in the paper entitled "$^{123}$I-Indocyanine Green ($^{123}$I-ICG) as an Agent for Dynamic Studies of the Hepato Biliary System" issued by the Brookhaven National Laboratory and having the number BNL-19084, and another paper entitled "Note on the distribution of iodine-123 labeled indocyanine green in the eye" issued by the Brookhaven National Laboratory having the number BNL-20123.

What is claimed is:

1. The method of labeling indocyanine green (ICG) with carrier-free iodine-123 comprising the steps of:
    a. condensing carrier-free $^{123}$Xe on dry crystals of substantially pure ICG in an evacuated anhydrous environment at a temperature below that of the boiling point of $^{123}$Xe under evacuated conditions in an amount sufficient to produce labeled ICG having a predetermined specific activity of $^{123}$I;
    b. permitting the $^{123}$Xe to decay at the aforesaid temperature for a sufficient amount of time to produce the aforesaid specific activity;
    c. removing any remaining $^{123}$Xe by warming the ICG to a temperature above that of the boiling temperature of said $^{123}$Xe;
    d. dissolving the remaining product;
    e. removing the remaining $^{123}$I from the dissolved product; and
    f. evaporating the dissolved product to dryness.

2. The method of claim 1 in which sufficient $^{123}$Xe is condensed to produce specific activity greater than 0.1 mCi of $^{123}$I per mg of ICG.

3. The method of claim 2 in which $^{123}$I remaining in the labeled ICG is removed by passing the dissolved ICG through an ion retardation resin.

4. The method of labelling indocyanine green (ICG) with carrier-free iodine-123 comprising the steps of:
   a. preparing a solution of ICG in sufficient methyl alcohol to dissolve all of said ICG at ambient conditions;
   b. removing any free iodide from the ICG by passing said solution through an iodide ion retardation resin;
   c. evaporating the alcohol to obtain crystalline ICG which is then vacuum dried at room temperature;
   d. condensing carrier-free $^{123}$Xe on dry crystals of the ICG in an evacuated anhydrous environment at a temperature below that of the boiling point of $^{123}$Xe under the evacuated conditions, in the amount sufficient to produce labeled ICG leaving a predetermined specific activity of $^{123}$I;
   e. permitting the $^{123}$Xe to decay at the aforesaid temperature for a sufficient amount of time to produce a predetermined amount of $^{123}$I;
   f. removing any remaining $^{123}$Xe by warming the ICG to a temperature above that of the boiling temperature of said $^{123}$Xe;
   g. dissolving the remaining product,
   h. removing the remaining $^{123}$I from the dissolved product
   i. evaporating the dissolved product to dryness.

* * * * *